United States Patent [19]

Goodman

[11] Patent Number: 4,900,675
[45] Date of Patent: Feb. 13, 1990

[54] MODULATION OF ANIMAL CELLULAR RESPONSES WITH COMPOSITIONS CONTAINING ISOXANTHOPTERIN-8-(1'-β-ALDO-GLYCOSIDYL) DERIVATIVES

[75] Inventor: Michael G. Goodman, Rancho Santa Fe, Calif.

[73] Assignee: Scripps Clinic and Research Foundation, La Jolla, Calif.

[21] Appl. No.: 154,991

[22] PCT Filed: Dec. 12, 1986

[86] PCT No.: PCT/US86/02716

§ 371 Date: Jan. 27, 1988

§ 102(e) Date: Jan. 27, 1988

[87] PCT Pub. No.: WO87/03617

PCT Pub. Date: Jun. 18, 1987

Related U.S. Application Data

[63] Continuation-in-part of Ser. No. 808,886, Dec. 13, 1985, which is a continuation-in-part of Ser. No. 798,629, Nov. 15, 1985, Pat. No. 4,746,651, which is a continuation of Ser. No. 546,679, Nov. 1, 1983, Pat. No. 4,643,992.

[51] Int. Cl.[4] .............................................. A61K 31/70
[52] U.S. Cl. .................................. 435/240.27; 514/43; 514/45
[58] Field of Search ...................... 435/240.27; 514/45, 514/43

[56] References Cited

U.S. PATENT DOCUMENTS 3,798,210 3/1974 Pfleiderer ..................... 260/211.5 R
4,643,992 2/1987 Goodman ....................... 435/240.27

OTHER PUBLICATIONS

Ziegler et al., "Participation/Pterins in the Control of Lymphocyte Stimulation and Lymphoblast Proliferation", *Cancer Research*, vol. 43, pp. 5356–5359, (Nov. 1983).
Goodman et al., Proc. Natl. Acad. Sci., vol. 78, pp. 7604–7608, 1981.
Chemical Abstracts, vol. 71, No. 25, Abstract No. 119619g, 1969.
Chemical Abstracts, vol. 98, No. 3, Abstract No. 15346g, 1983.
Chemical Abstracts, vol. 99, No. 5, Abstract No. 36854g, 1983.
Goodman et al., J. Immunology, vol. 128, p. 2399–2404, 1982.

*Primary Examiner*—Peter D. Rosenberg
*Attorney, Agent, or Firm*—Dressler, Goldsmith, Shore, Sutker & Milnamow, Ltd.

[57] ABSTRACT

Animal cellular responses, and particularly immune-related responses, are modulated by contacting such cells with a unit dose of a composition containing an effective amount of an isoxanthopterin-8-aldoglycoside. An isoxanthopterin has a structure that conforms to the formula

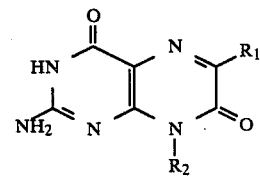

wherein $R_1$ is a substituent and $R_2$ is an aldoglycoside.

18 Claims, No Drawings

MODULATION OF ANIMAL CELLULAR RESPONSES WITH COMPOSITIONS CONTAINING ISOXANTHOPTERIN-8-(1'-β-ALDOGLYCOSIDYL) DERIVATIVES

CROSS-REFERENCE TO COPENDING APPLICATION

This is a continuation-in-part of copending patent application Ser. No. 808,886 filed Dec. 13, 1985, which is a continuation-in-part of Ser. No. 798,629, filed Nov. 15, 1985, now U.S. Pat. No. 4746651, which is itself a continuation of copending patent application Ser. No. 546,679, filed Nov. 1, 1983, now U.S. Pat. No. 4,643,992.

TECHNICAL FIELD

The present invention relates to modulation of animal cellular responses, and more particularly, to modulation of antigen-specific immune and other animal cellular responses by compositions containing a low molecular weight derivative of isoxanthopterin.

BACKGROUND ART

An animal's immune system is comprised of numerous elements that act separately and/or in concert to counteract, to eliminate, or to neutralize substances that are recognized by that system as foreign to the animal host. Generally, but not necessarily, the substance recognized as foreign by the immune system has its origin exogenous to the host. Exemplary of such exogenous substances are infectious bacteria and the by-products of their cellular activity, virus particles and their proteins, proteins injected by insect stings, and the like. In autoimmune diseases, such as rheumatoid arthritis, the host's immune system perceives host-made proteins or self-made proteins as foreign.

The principal effectors of the immune system are the leukocytes, which include lymphocytes of thymic origin (T cells), lymphocytes produced in bone marrow (B cells), neutrophils which, inter alia, produce enzymes that make oxidizing agents such as hydrogen peroxide that have cytotoxic effects upon bacteria, and macrophages, which present the foreign substance or immunogen (antigen) to the T cells and B cells, as well as produce a protein designated interleuken-1 that assists T cell transformation into T helper cells and B cell and T cell proliferation. Complement, which is a complex mixture of proteins that acts in an ordered, cascading manner upon the foreign substance, also plays a major role in immune responses.

B cells can be distinguished from T cells, inter alia, by the presence of monomeric immunoglobulins (antibodies) on their surface membranes. Mature B cells secrete antibodies into their environment when properly activated.

There are five known classes of immunoglobulins, identified as IgA, IgD, IgE, IgG, and IgM on the basis of five antigenically different heavy chain proteins that make up a portion of the immunoglobulin molecule. B cells also bear non-immunoglobulin cell markers, including a complement receptor (CR), a receptor for the Fc portion of immunoglobulin (FcR), I-region associated antigens (Ia), and a set of differentiation antigens (Lyb 1-7) that are identified by antisera and other means are correlated with various aspects of B cell maturation and activation. These markers are useful in phenotypically identifying B cells and B cell subpopulations.

While the immunoglobulins act upon the foreign substances, or antigen, the T cells, and particularly helper T cells, are believed necessary to stimulate B cells to divide and to differentiate into antibody secreting cells for humoral immunity. Suppressor T cells contribute to the regulation of humoral immunity, while cytotoxic T cells and T cell mediators of delayed-type hypersensitivity are the principal effectors of cell-mediated immunity.

Murine T cells bear surface antigens designated Lyt 1, 2, and 3 as well as L3T4 that are related to T cell functions. Helper T cell precursors are of the Lyt $1^+$, $2^-,3^-$L3T$4^+$ phenotype. These cells normally participate in the activation and regulation of B cells.

Helper T cells are known to assist in activation and differentiation of immunoglobulin-secreting B cells after a first message is received by the B cells from the activating immunogenic (antigenic) agent usually presented to it after processing by an antigen-presenting cell. However, the mode by which the T cells provide help for activation and differentiation of the B cells is a matter of controversy.

The immune response exhibited by animal cells can be modified by artificial suppression (immunosuppression) or enhancement (immunopotentiation). Artificially induced immunosuppression can be achieved by six general methods: (1) administration of a suppressive dose of antigen, (2) administration of specific antisera or antibodies, (3) use of other biologic reagents such as antilymphocyte antisera, (4) use of drugs or hormones, (5) radiation, and (6) surgical removal of lymphoid tissue. Immunopotentiation can be achieved by administration of an agent effecting (1) an increase in the rate at which the immune response develops, (2) an increase in the intensity or level of the response, (3) a prolongation of the response, or (4) the development of a response to an otherwise non-immunogenic substance.

The agents that are known to enhance immune responses are generally termed adjuvants and can be placed into two general categories: (1) those providing general potentiation; i.e., substances that enhance cellular and/or humoral immune responses for a wide variety of antigens, and (2) those providing specific potentiation; i.e., substances that enhance specific responses only to certain antigens.

Substances that can act as adjuvants can be grouped into the following categories: (1) water and oil emulsions, e.g., Freund's adjuvant, (2) synthetic polynucleotides and other polyanions, (3) hormones, drugs and cyclic nucleotides, (4) microbial products, e.g., endotoxins, (5) lymphokines and monokines such as the interleukins, and (6) synthetic peptides, e.g., bestatin and tuftsin.

A substance capable of specifically potentiating the immune response is transfer factor, a dialyzable leukocyte extract (DLE) obtained from human peripheral leukocytes. It has been reported that the transfer factor exhibits some effectiveness in patients with immunodeficiencies and possible effectiveness in cancer patients and in patients with limited immunodeficiencies. However, the efficacy of this agent is highly controversial, and much remains to be learned about it.

In some diseases and physiological conditions such as X chromosome-linked agammaglobulinemias, senescence and drug-induced-immunosuppression, B cell activation and differentiation is lacking or exists only at a reduced level, thereby lessening the immune response capabilities of the host. These diseases and conditions are representative of immunosuppressed states. Here, enhanced B cell activation and differentiation, if it can be effected, tends to beneficially lessen the immunological deficits that can manifest themselves as disease and/or improve the patient's condition.

An immunopotentiated state can be illustrated by the bodily condition after vaccination. Here, the immune response is first enhanced due to a primary response to the vaccine's immunogen, and usually can be beneficially enhanced still further by a "booster" injection of the immunogen or vaccine, administered later to provide an improved degree and/or duration of immunity.

Lymphokines and monokines are immunopotentiating proteins produced by lymphocytes and cells of the monocyte-macrophage lineage, respectively. One monokine, interleukin-1, is produced by macrophages when they are stimulated by a mitogen or antigen. Interleukin-1 is usually required for producing a primary antigenic response.

Interleukin-1 assists in the production of interleukin-2 by T cells. Interleukin-2 is a growth factor for T cells and assists in the transformation of helper T cells. Thus, induction of interleukin-1 production or of a protein-responsive activity or T cells similar to that produced by interleukin-1 would be beneficial in enhancing immune responses, particularly where macrophages are absent or where their production of monokines is deficient.

Co-assigned U.S. Pat. No. 4,539,205 to Goodman and Weigle describes modulation of animal cellular responses with 8-substituted guanine derivatives bonded 9-1' to an aldose having 5 or 6 carbon atoms in the aldose chain (ring). The cellular modulations described in that patent relate mostly to immunomodulation such as adjuvanticity in producing primary and secondary immune responses. Activity against certain neoplastic conditions is also disclosed as are T cell-replacing activity, an IL-1 like activity on thymocytes, and induction of the release of lysosomal enzymes from neutrophils. The 8-substituents in those molecules have electron withdrawing inductive effects relative to hydrogen. Thus, halo, mercapto or its thioxo tautomer, acyl mercapto, alkyl sulfido, nitro, cyano, keto, halomethyl and methyleneoxy alkyl and the like were disclosed as useful, while electron donating substituents such as an amino group were found to be inactive.

In addition, co-assigned, co-pending U.S. patent application Ser. No. 546,679 and its corresponding published European patent application No. 83306791.1 further discloses the use of derivatives of 8-hydroxyguanine (8-oxoguanine), 7-methyl-8-oxoguanine and 7-methyl-8-thioxo-guanine in modulating animal cellular responses. Further results using guanine derivatives disclosed in U.S. Pat. No. 4,539,205 are also disclosed as are similar results using guanine derivatives disclosed for the first time in that application.

U.S. Pat. No. 3,798,210 to Pfleiderer describes the synthesis of 8-(1'-glycosidyl)pteridines, including isoxanthopterin derivatives. That patent teaches the use of its compounds as the active pharmaceutical agents against specific pathogens such as malaria and tubercle bacilli, pathogenic fungi, gram-positive and gram-negative bacteria, and primarily against viruses such as herpes virus and influenza virus. Some of the compounds of the Pfleiderer patent are also useful herein, but not as antibiotics as is taught in Pfleiderer. This use is described hereinafter.

BRIEF SUMMARY OF THE INVENTION

Animal cellular responses are modulated by contacting animal cells with a composition containing a diluent amount of a physiologically tolerable carrier admixed with an effective amount of an active ingredient that is an isoxanthopterin derivative. The structure of the isoxanthopterin derivative conforms to that of the formula

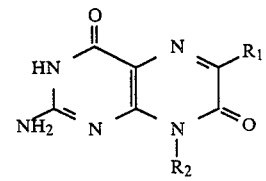

wherein $R_1$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo (O=), lower alkoxy, phenyl-lower alkoxy, halo, mercapto, thioxo (=), lower alkylthio, lower alkyloylthio, phenyl-lower alkylthio, lower alkanoyl (lower acyl), carboxy, lower alkoxy carbonyl, lower alkylcarboxy, lower alkylene lower alkylcarboxylate, lower alkoxy lower alkyl carbonyl, and carboxamido and lower alkyl carboxamido in which the carboxamido group has the formula $CONR_3R_4$ wherein $R_3$ and $R_4$ are the same or different and are selected from the group consisting of hydrogen and lower alkyl or $NR_3R_4$ together form a heterocyclic ring having five or six atoms in the ring;

$R_2$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent, if present on one oxygen, is present on all available ring substituent oxygens;

the pharmaceutically acceptable salts of the isoxanthopterin derivative; and the tautomers of the isoxanthopterin derivative.

The contact between the cells and the composition is maintained for a period of time sufficient for modulation of the contacted cells' responses.

Enhancement of immunogen(antigen)-specific humoral immune responses resulting in adjuvanticity that provides enhanced antibody secretion in the presence of immunogen is a particular example of the animal cellular response than can be modulated in accordance with the present invention. The term "modulate" in its various grammatical forms, as used herein, designates enhancement as well as inhibition of an animal cellular response in vitro and/or in vivo.

A cellular response-modulating composition of this invention can be used to provoke differing, although related results depending, inter alia, upon the manner of administration, dosage and the cell population to which it is administered. The active ingredient isoxanthopterin derivative can be present in the composition admixed in the carrier as a suspension of solid isoxanthopterin derivative in a solid or liquid carrier, or as a dissolved solute in the carrier.

Contacting leukocytes such as B lymphocytes with a composition of this invention and maintaining that contact for a predetermined period of time modulates the immune response of those leukocytes. Modulation of B lymphocyte (B cell) responses can be effected by treating B cells with an effective amount of the immunogen to form immunogen-primed B cells, followed by contacting the B cells with the immune response-modulating composition and a further effective amount of immunogen. B cell immune responses can also be modulated by contacting the B cells with a priming immunogen and an immune response-modulating composition of this invention followed thereafter by contacting the immunogen primed cells with an additional effective amount of the immunogen alone, or with a further amount of immune response-modulating composition. In addition, an immune response-modulating composition can be administered to contact the animal cells and thereafter followed, while the isoxanthopterin derivative is in contact with the animal cells; i.e., present in vivo or in vitro, with one or more immunizing doses of an immunogen. These cell response modulations are within those effects referred to as adjuvanticity; i.e., the isoxanthopterin derivative acts as an adjuvant for the immunogen, and thus provides an immunogen- or antigen-specific modulation.

The methods of this invention can be used on cells in vivo as well as in vitro. The compositions can be administered subcutaneously, intravenously intraperitoneally in a liquid form, or perorally as in pill or capsule form, or in liquid form as a slurry, suspension or solution.

The present invention has several benefits and advantages.

One of the benefits of this invention is that its use can provide the "second message" required for B lymphocyte activation and differentiation in response to a first, priming (immunogenic) message.

An advantage of this invention is that contacting animal cells as described herein can lead to the activation and differentiation of those cells, which in turn can lead to the induction of protein production, as in the case of immunoglobulin (antibody) secretion from B cells, monokine secretion from macrophages, and lymphokine secretion from T cells.

Another advantage of the present invention is that enhanced immune responses can be effected in both the presence and absence of T helper cell activity. Thus, enhanced immune responses are noted in both T cell-dependent and T cell-independent systems, making this invention useful when host leukocytes are immunocompromised from having lost T helper cell function, as well as in leukocytes with normal T helper function.

Still further benefits and advantages of the present invention will be apparent to those skilled in the art from the Detailed Description that follows.

DETAILED DESCRIPTION OF THE INVENTION

A. Isoxanthopterin-8-Aldoglycosides

2-Amino-4-hydroxypteridine and its derivatives are known in the art as pterin and its derivatives, respectively. Prototropically active pterins are usually represented in their most favored tautomeric formula as 2aminopterin-4-one and its derivatives. Pfleiderer, Chapter 2.16 in *Comprehensive Heterocyclic Chemistry*, Vol. 3, Part 2B, Katritzky and Rees eds., Pergamon Press, New York (1984) pages 63–327.

2-Amino-4,7-dihydroxypteridine and its tautomer 2-aminopterin-4,7-dione are known as isoxanthopterin. A more precise chemical name for isoxanthopterin is 2-amino-3,4,7,8-tethydro-4,7-dioxopteridine. The compounds useful herein will generally be referred to as isoxanthopterin and its derivatives. These useful isoxanthopterin derivatives all possess an aldoglycoside (sugar aldehyde) as a substituent at the 8-position of the pteridine ring system, and can also include a substituent other than hydrogen at the 6-position.

Isoxanthopterin and 6-substituted isoxanthopterins for preparation of the isoxanthopterin derivatives useful herein are themselves readily prepared by known reactions. In one reaction scheme, a 2,5,6-triamino-4-hydroxypyrimidine is reacted with an alpha-keto acid in which a substituent beta to the carboxy group forms the $R_1$ group in the structural formulas herein. See, Hurst, *An Introduction To The Chemistry And Biochemistry Of Pyrimidines, Purines And Pteridines*, John Wiley & Sons, New York, pages 86–103 (1980), and the citations therein. In another reaction scheme, the above pyrimidine is reacted with a di-lower alkyl ester of an acetylene dicarboxylic acid to form a lower alkyl carboxylic acid at the 6-position and lower alkyl esters thereof. Iwanami, *Bull. Chem. Soc. Japan*, 44:1314 (1971). Still further compounds and reaction schemes are discussed in Pfleiderer, Chapter 2.16 of *Comprehensive Heterocyclic Chemistry*, supra.

The isoxanthopterin 8-aldoglycoside derivatives useful herein are preferably prepared from isoxanthopterin or a 6-substituted isoxanthopterin derivatives to which the aldoglycosidic group is thereafter added by the method of Pfleider as described in U.S. Pat. No. 3,798,210, whose disclosures are incorporated herein by reference. Other methods of preparation such as the cyclization of a 2-amino-3,4-dihydro-5-nitro-4-oxo-6-aminoglysidyl-pyrimidine described by Lohrmann and Forrest, *J. Chem. Soc.*, 460–465 (1965) are also useful.

Briefly, in accordance with the Pfleider technique, a suitably substituted isoxanthopterin is O-metalized at the 7-position with a quadrivalent metal of the fourth main group and third to fifth period of the periodic system. The O-metalized compound so prepared is reacted with an aldoglycoside whose 1'-position hydroxyl group is itself derivatized as a reactive ester such as an ester of a lower carboxylic acid ester like acetic acid, or as an ether such as a lower alkyl ether like a methyl ether. The 1'-position hydroxyl can also be replaced by a halo group such as bromide as taught by Pfleider and his co-workers in *Chem. Ber.*, 106, 317–331 (1973); *Chem. Ber.*, 106, 1952–1975 (1973); and *Chem. Ber.*, 107, 339–361 (1974).

Quadrivalent germanium, tin and especially silicon are preferred O-metalizing agents. The particularly preferred metalizing agent is hexamethyldisilazane.

A strong acid catalyst such as an inorganic acid like sulfuric acid is preferably used with an O-metalizing agent such as hexamethyldisilazane. The hexamethyldisilazane is preferably utilized in excess, in the absence of water, and preferably in the presence of nitrogen or argon rather than air.

The 7-O-metalized isoxanthopterin is thereafter typically collected and reacted in an inert solvent such as dry benzene with the aldoglycoside whose hydroxyl groups other than that of the 1'-position are protected, as by benzoyl or acetyl groups. The 1'-position of the chosen aldoglycoside is protected as before discussed.

The glycosidation reaction is preferably carried out in the presence of a mercuric salt such as a mercuric halide, or mixture of mercuric halides where an aldoglycosidyl 1'-ether or 1'-ester is used. An elevated temperature such as that of refluxing benzene at one atmosphere of pressure is used for the aldoglycosylation reaction (condensation of sugar and isoxanthopterin).

The mercury salt, where used, is filtered from the reaction medium once the reaction is over, and the isoxanthopterin-8-(hydroxy protected)-aldoglycoside) derivative is recovered as by column chromatography. The hydroxy protecting groups, e.g., benzoyl or acetyl, are thereafter removed by standard procedures such as reaction in sodium methoxide-methanol, followed by neutralization. The desired isoxanthopterin-8-(1'-aldoglycoside derivative is thereafter collected and purified, as by crystallization.

Useful isoxanthoperin derivatives have a structure that corresponds to the formula

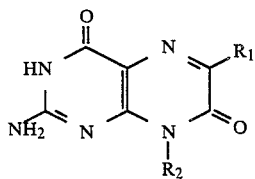

wherein $R_1$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy oxo (O=), lower alkoxy, phenyl-lower alkoxy, halo, mercapto, thioxo (S=), lower alkylthio, lower alkyloylthio, phenyl-lower alkylthio, lower alkanoyl (lower acyl), carboxy, lower alkoxy carbonyl, lower alkylcarboxy, lower alkylene lower alkylcarboxylate, lower alkoxy lower alkyl carbonyl, and carboxamide and lower alkyl carboxamide in which the carboxamido group has the formula $CONR_3R_4$ wherein $R_3$ and $R_4$ are the same or different and are selected from the group consisting of hydrogen and lower alkyl or $NR_3R_4$ together form a heterocyclic ring having five or six atoms in the ring;

$R_2$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent, if present on one oxygen, is present on all available ring substituent oxygens;

the pharmaceutically acceptable salts of the isoxanthopterin derivative; and the tautomers of the isoxanthopterin derivative.

Groups and radicals are referred to as "lower" denote that they possess 1 to about 6 carbon atoms, and preferably 1 to about 3 carbon atoms.

Lower alkyl radicals include, for example, methyl, ethyl, propyl, iso-propyl, n-butyl, sec-butyl, t-butyl, n-pentyl, 2-methyl-3-butyl, 1-methylbutyl, 2-methylbutyl, neo-pentyl, n-hexyl, 1-methylpentyl, 3-methylpentyl, 1-ethylbutyl, 2-ethylbutyl, 2-hexyl, 3-hexyl, and the like.

Hydroxy lower alkyl radicals include hydroxy methyl, 2-hydroxyethyl, 2-hydroxypropyl, 3-hydroxypropyl, 3-hydroxy-2-butyl, 3-hydroxy-2,2-dimethylpropyl, 6-hydroxyhexyl and the like.

Polyhydroxy lower alkyl radicals include 1,2-dihydroxyethyl, 1,2,3-trihydroxypropyl, 2,3-dihydroxypropyl, 3,4-dihydroxybutyl and the like. Those skilled in the art will understand that the contemplated polyols contain no more than one hydroxyl group on each carbon atom of the lower alkyl group.

Phenyl-lower alkyl radicals include phenyl-substituted lower alkyl radicals listed above, wherein the alkyl position of the radical is bonded to the 6-position of the isoxanthopterin 8-aldoglycoside. Exemplary radicals include benzyl, phenethyl, 2-phenylpropyl, 2-phenyl-3-methylpentyl and the like.

Lower alkyl phenyl radicals are the above-described lower alkyl radicals substituted on a phenyl radical that is itself bonded to the 6-position of an isoxanthopterin 8-aldoglycoside. Exemplary of such lower alkyl phenyl radicals are o-xylyl, p-(2-hexyl)phenyl, m-(iso-propyl)-phenyl, and the like. Trifluoromethylphenyl substituted ortho, meta or para to the position of binding to the 6-position of the isoxanthopterin constitute a sub-class of lower alkyl phenyl radicals.

Lower alkoxy phenyl radicals can be viewed as lower alkyl ethers of ortho-, meta- or para-isoxanthopterin substituted phenols, wherein the lower alkyl group is as described before. Exemplary lower alkoxy phenyl radicals include o-methoxyphenyl, m-sec-butoxyphenyl, and p-(2-ethylbutoxy)phenyl.

Halophenyl radicals utilize halogen-substituted phenyl radicals in which the halogen is preferably fluoro, chloro and bromo, and also include iodo. Exemplary radicals include o-chlorophenyl, p-fluorophenyl and m-bromophenyl.

Hydroxy and mercapto radicals are also referred to herein as oxo and thioxo radicals, respectively, due to their tautomer formation.

Lower alkoxy radicals can be viewed as ethers formed from a 6-hydroxy isoxanthopterin and a before-described lower alkyl group. Exemplary radicals include methoxy, ethoxy, propoxy, iso-propoxy, n-butoxy, and the like. Phenyl-lower alkoxy radicals can similarly be viewed as ethers formed from a 6-hydroxy isoxanthopterin and a before-described phenyl-lower alkyl radical. Exemplary of these materials are benzyloxy, 2-phenylethoxy, 2-phenylpropoxy and the like.

Halo radicals preferably include chloro, bromo, as well as fluoro and iodo.

Lower alkylthio and phenyl-lower alkylthio radicals are sulfide ethers and are thus analogous to the oxygen ethers described above, as lower alkoxy and phenyl-lower alkoxy radicals, respectively.

A carboxy radical is a carboxylic acid ($-CO_2H$) bonded to the 6-position of the isoxanthopterin 8-aldoglycoside. A lower alkoxy carbonyl radical can be viewed as an ester of a 6-carboxy isoxanthopterin formed with a lower alkyl alcohol where the lower alkyl portion of the alcohol is a lower alkyl radical as before-described. Exemplary esters are ethyl, methyl, t-butyl, neo-pentyl carboxylates, and the like. These esters can also be named ethoxycarbonyl, methoxycarbonyl, t-butoxycarbonyl and neo-pentoxycarbonyl, respectively.

Lower alkyl carboxy radicals are the before-described lower alkyl radicals that further include a carboxy group. Lower alkoxy lower alkyl carbonyl radicals can be viewed as esters of substituent lower alkyl carboxy radicals with lower alkyl alcohols, which are described immediately above. Exemplary lower alkyl carboxy radicals include carboxymethyl, 2-carboxyethyl, 2-carboxyhexyl and the like. Exemplary lower alkoxy lower alkyl carbonyl radicals include 3-isopropoxycarbonylpropyl, 4-hexyloxycarbonylpentyl, and the like.

Carboxamido and lower alkylcarboxamido radicals can be viewed as being formed from a carboxy or a lower alkyl carboxy substituent, respectively, and an amine. The carboxamido group has the formula $CONR_3R_4$ wherein $R_3$ and $R_4$ are the same or different and are selected from the group consisting of hydrogen and lower alkyl. Alternatively, $NR_3R_4$ together can form a heterocyclic ring having five or six atoms in the ring. Exemplary useful amines include methylamine, propyl-amine, sec-butylamine, hexylamine, dimethylamine, methylethylamine, butylhexylamine, pyrrolidine, morpholine, piperidine, pyrrole and 4-methylpiperazine. Unsubstituted carboxy amides (where $R_3$ and $R_4$ are hydrogen) are formed from ammonia as the amine.

Lower alkanoyl radical substituents, also known as lower acyl radicals, contain a carbonyl group bonded directly to the 6-position of the isoxanthopterin ring thereby making the compounds ketones, or an aldehyde, as is appropriate. Exemplary lower alkanoyl groups include formyl, acetyl, propionyl, 2-methylpropionyl, butyryl, 3-methylvaleryl and the like. The acyl carbon of the radical is considered a part of the "lower" alkanoyl or acyl group.

Lower alkyloylthio or lower acylthio radicals can be viewed as thioesters formed from an appropriate 6-mercapto substituent of an isoxanthopterin derivative and a lower alkyl carboxylic acid. Exemplary of such radicals are thioacetyl, thiopropionyl, thiohexanoyl and the like.

A lower alkylene lower alkylcarboxylate radical can be viewed as an ester of a substituent hydroxy lower alkyl radical and a lower alkyl carboxylic acid. Exemplary hydroxy lower alkyl substituents have been discussed previously, as have the lower alkanoyl (lower acyl) portions of lower alkyl carboxylic acids that can be present in such esters.

The isoxanthopterin 8 aldoglycosides are weak bases, and as such can form acid addition salts. Pharmaceutically acceptable, non-toxic acid addition salts of isoxanthopterin derivatives are useful herein, and can be formed by treatment of the isoxanthopterin 8-aldoglycoside with an appropriate acid. Exemplary inorganic acids include hydrochloric, hydrobromic, sulfuric, phosphoric and the like acids. Exemplary orgainic acids include acetic, propionic, glycolic, pyruvic, malonic, succinic, maleic, fumaric, malic, tartaric, citric, benzoic, cinnamic, mendelic, methansulfonic, ethanesulfonic, benzenesulfonic, p-toluenesculfonic, salicyclic, p-aminosalicyclic and the like acids. Conversely, the acid addition salt form can be converted to the free base form by treatment with alkali.

Useful isoxanthopterin derivatives also include 6-substituted carboxylic acids and lower alkyl substituted carboxylic acids, as already noted. Basic salts of those carboxylic acids are also contemplated, and are formed by treatment of the carboxylic acid with an appropriate alkaline reagent to form a 6-isoxanthopterin 8-aldoglycoside carboxylate cation salt. Exemplary non-toxic cation salts of such carboxylic acids include sodium, potassium, zinc, aluminum, calcium, magnesium, and the like.

The 8-aldoglycoside portion ($R_2$) of the useful isoxanthopterin derivatives are cyclic, contain 5 or 6 carbon atoms, and are selected from the group consisting of 1'-aldopentosidyl, 1'-aldohexosidyl, mono-deoxygenated 1'-aldopentosidyl, and mono-deoxygenated-1'-aldohexosidyl radicals.

Exemplary 1'-aldopentosidyl radicals are the 1'-radicals of ribose, arabinose, lyxose and xylose that are named 1'-ribofuranosidyl, 1'-arabinofuranosidyl, 1'lyxofuranosidyl, and 1'xylofuranosidyl radicals, respectively. Exemplary 1-aldohexosidyl radicals are the 1'-radicals of glucose, galactose, mannose, gulose, allose, altrose, and rhamnose that are named 1'-glucopyranosidyl, 1'-galactopyranosidyl, 1'-mannopyranosidyl 1'-gulopyranosidyl, 1'-allopyranosidyl, 1'-altropyranosidyl, 1'-rhamnopyranosidyl, radicals, respectively. An exemplary mono-deoxygenated 1'-aldopentosidyl radical is that of deoxyribose that is named the 1'(2'-deoxy)-ribofuranosidyl radical. An exemplary mono-deoxygenated 1'-aldohexosidyl radical is that of deoxygulose, named the 1'-(2'-deoxy)gulopyranosidyl radical.

Useful aldoglycosidyl radicals can have one or more hydroxyl groups esterified by a lower alkanoyl radical such as formyl, acetyl, propionyl or hexanoyl, and also by a benzoyl radical. Aldoglycosidyl radicals are also useful when etherified by lower alkyl, especially methyl and ethyl radicals, while benzyl ethers are also useful.

Suitable aldoglycosidyl radicals conform to the formula

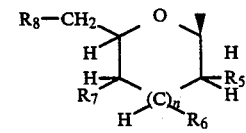

wherein n is one or zero;

$R_5$ is hydrogen, hydroxy, lower alkoxy such as methoxy and ethoxy (and others as described before), benzyloxy, lower alkanoyloxy such as formyloxy, acetoxy (and other lower alkyl carboxylate radicals as are described before) or benzoxy.

$R_6$ when present, as well as $R_7$ and $R_8$ are all the same. These radicals can be hydroxy, a lower alkyl ether (lower alkoxy) such as methoxy and ethoxy, a benzyl ether (benzyloxy), a lower alkanoyl radical (lower acyl) such as formyloxy, acetoxy, or a benzoate ester (benzoxy). When $R_5$ is other than hydrogen, $R_5=R_6$ when present$=R_7=R_8$. Thus, an O-substituent, when present on one oxygen is present on all available ring substituent oxygens.

The bonds of the above formula are not intended to convey any particular stereo specific configuration, except at the 1'-position at which the beta anomer is indicated.

In preferred practice, the aldoglycosidyl radical is selected from the group consisting of 1'-ribofuranosidyl, 1'-glucopyranosidyl, and 1'-(2'-deoxy)ribofuranosidyl radicals. Thus, preferably, when n is zero and $R_5$, $R_7$ and $R_8$ are all hydroxy, $R_6$ is absent, the aldoglycosidyl radical is selected from the group consisting of 1'-ribofuranosidyl; when n is zero, $R_5$ is hydrogen and $R_7$ and $R_8$ are hydroxy, $R_6$ is absent, the aldoglycosidyl radical is 2'-deoxy-1'-ribofuranosidyl; and when n is 1, and $R_5=R_6=R_7=R_8=$hydroxy, 1'-glucopyranosidyl is the aldoglycosidyl radical.

As already noted, the aldoglycoside is bonded from its 1'-position to the 8-position of the isoxanthopterin derivative. When named as an isoxanthopterin derivative, that bonding can be described as an 8-1' bond. The beta anomer of the aldoglycoside is that preferred herein, although mixtures of alpha and beta anomers are also useful. The aldoglycoside utilized is in the D stereo configuration and that configuration is implied where it is not stated.

Structural formulas of exemplary isoxanthopterin derivatives useful in the method of this invention are shown below, wherein $R_1$ and $R_2$ are as shown in the Table following the structural formula.

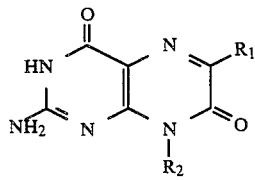

TABLE

| $R_1$ | $R_2$ |
|---|---|
| methyl | 1'-arabinofuranosidyl |
| iso-propyl | 1'-lyxofuranosidyl |
| n-butyl | 1'-ribofuranosidyl |
| t-butyl | 1'-(2'-deoxy)ribofuranosidyl |
| neo-pentyl | 1'-xylofuranosidyl |
| n-hexyl | 1'-gulopyranosidyl |
| benzyl | 1'-galactopyranosidyl |
| phenethyl | 1'-mannopyranosidyl |
| 2-phenylpropyl | 1'-(2',3',4',6'-tetra-O—acetyl)glucopyranosidyl |
| 2-phenyl-3-methylpentyl | 1'-(2',3',5'-tri-O—acetyl)-ribofuranosidyl |
| o-xylyl | 1'-(2',3',5'-tri-O—acetyl)-arabinofuranosidyl |
| p-(2-hexyl)phenyl | 1'-(2'-deoxy-3',5'-di-O—methyl)ribofuranosidyl |
| m-(iso-propyl)phenyl | 1'-(2',3',4',6'-tetra-O—ethyl)glucopyranosidyl |
| p-(trifluoromethyl)phenyl | 1'-(2',3',5'-tri-O—benzyl)-ribofuranosidyl |
| o-methoxyphenyl | 1'-(2',3',5'-tri-O—benzoyl)-ribofuranosidyl |
| m-sec-butoxyphenyl | 1'-(2',3',4',6'-tetra-O—ethyl)glucopyranosidyl |
| p-(2-ethylbutoxy)phenyl | 1'-(2'-deoxy-3',5'-di-O—methyl)ribofuranosidyl |
| o-chlorophenyl | 1'-gulopyranosidyl |
| m-bromophenyl | 1'-allopyranosidyl |
| p-fluorophenyl | 1'-altropyranosidyl |
| hydroxy | 1'-rhamnopyranosidyl |
| mercapto | 1'-galactopyranosidyl |
| methoxy | 1'-glucopyranosidyl |
| iso-propoxy | 1'-xylofuranosidyl |
| n-hexyloxy | 1'-(2'-deoxy)ribofuranosidyl |
| benzoxy | 1'-ribofuranosidyl |
| 2-phenylethoxy | 1'-lyxofuranosidyl |
| 2-phenylpropoxy | 1'-(2'-deoxy)gulopyranosidyl |
| chloro | 1'-glucopyranosidyl |
| bromo | 1'-(2'-deoxy)ribofuranosidyl |
| fluoro | 1'-ribofuranosidyl |
| iodo | 1'-ribofuranosidyl |
| ethylsulfido | 1'-glucopyranosidyl |
| benzylsulfido | 1'-arabinofuranosidyl |
| carboxy | 1'-lyxofuranosidyl |
| carbomethoxy | 1'-ribofuranosidyl |
| carbethoxy | 1'-(2'-deoxy)ribofuranosidyl |
| carbo-t-butoxy | 1'-xylofuranosidyl |
| neo-pentoxycarbonyl | 1'-glucopyranosidyl |
| 2-carboxyethyl | 1'-galactopyranosidyl |
| 4-carboxybutyl | 1'-mannopyranosidyl |
| ethyl carboxymethyl | 1'-(2',3',4',6'-tetra-O—acetyl)glucopyranosidyl |
| sec-butyl carboxyethyl | 1'-(2',3',5'-tri-O—acetyl)-ribofuranosidyl |
| sodium carboxy | 1'-(2',3',5'-tri-O—acetyl)-arabinofuranosidyl |
| hydroxymethyl | 1'-(2',3',5'-tri-O—methyl)-ribofuranosidyl |
| 2-hydroxyethyl | 1-(2',3',4',6'-tetra-O—benzyl)allopyranosidyl |
| 1,2-dihydroxyethyl | 1'(2'-deoxy)gulopyranosidyl |
| 1,2,3-trihydroxypropyl | 1'-rhamnopyranosidyl |

Particularly preferred isoxanthopterin 8-aldoglycosides are those having hydrogen, hydroxy, lower alkyl such as methyl, carboxy and lower alkyl carboxylate such as ethyl or methyl carboxylate (ethoxycarbonyl or methoxycarbonyl) and polyhydroxy lower alkyl bonded at the 6-position, in which the 8-aldoglycoside portion of the molecule is beta-1-ribofuranosidyl, beta-1'-(2'-deoxy)ribofuranosidyl, and beta-1'-glucopyranosidyl. Exemplary of such particularly preferred materials are:

8-(1'-beta-D-ribofuranosidyl)isoxanthopterin;
8-(1'-beta-D-2'-deoxyribofuranosidyl)isoxanthopterin;
8-(1'-beta-D-glucopyranosidyl)isoxanthopterin;
6-hydroxy-8-(1'-beta-D-ribofuranosidyl)isoxanthopterin;
6-hydroxy-8-(1'-beta-D-2'-deoxyribofuranosidyl)-isoxanthopterin; 6-hydroxy-8-(1'-beta-D-glucopyranosidyl) isoxanthopterin;6-methyl-8-(1'-beta-D-ribofuranosidyl)isoxanthopterin; 6-methyl-8-(1'-beta-D-glucopyranosidyl)isoxanthopterin;
6-methyl-8-(1'-beta-D-2'-deoxyribofuranosidyl)isoxanthopterin; 6-carboxy-8-(1'-beta-D-ribofuranosidyl)-isoxanthopterin; 6-carboxy-8-(1'-beta-D-glucopyranosidyl)isoxanthopterin; 6-carboxy-8-(1'-beta-D-2'-deoxyribofuranosidyl)isoxanthopterin; 6-methoxycarbonyl-8-(1'-beta-D-ribofuranosidyl)isoxanthopterin; 6-methoxycarbonyl-8-(1'-beta-D-2'-deoxyribofuranosidyl)isoxanthopterin; and
6-methoxycarbonyl-8-(1'-beta-D-glucopyranosidylisoxanthopterin.

Most preferred isoxanthopterin derivatives useful in the method of this invention are those compounds in which $R_2$ is the 1'-D-ribofuranosidyl radical, and in which $R_1$ is selected from the group consisting of hydrogen, methyl and carboxy. These compounds have structures that conform to the formula

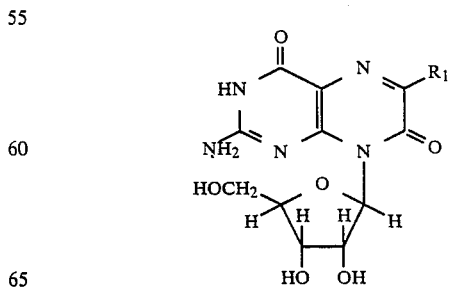

wherein $R_1$ is selected from the group consisting of hydrogen, methyl and carboxy.

b. Contacting Compositions

The active ingredient isoxanthopterin derivative used in the present invention is contacted with animal cells whose responses are to be modulated in vitro in cell culture or in vivo by administration to an animal perorally or parenterally in customary dosage unit compositions, that is, as compositions in unit dosage form comprising a physiologically tolerable carrier admixed with an effective dosage unit of the isoxanthopterin derivative.

The term "unit dosage" and its grammatical equivalents as used herein refer to physically discrete units suitable as unitary dosages for human patients and other warm blooded animals, each unit containing a predetermined effective amount of the active ingredient calculated to produce the desired therapeutic effect in association with the required physiologically tolerable carrier, e.g. a diluent of a vehicle. The specifications for the novel unit dosage forms of this invention are dictated by and are directly dependent on (a) the unique characteristics of the active isoxanthopterin derivative ingredient and the particular therapeutic effect to be achieved, and (b) the limitations inherent in the art of compounding such an active ingredient for therapeutic use in vitro, as well as in vivo in humans and other animals.

Examples of suitable unit dosage forms in accord with this invention are tablets, capsules, pills, powder packets, granules, wafers, and the like, segregated multiples of any of the foregoing, as well as liquid solutions, emulsions and suspensions. Liquid compositions can be administered in usual manners such as subcutaneously, intraperitoneally, intermuscularly, perorally or the like.

The amount of active ingredient that is administered in vivo depends on the age and weight of the patient, the particular condition to be treated, the frequency of administration, and the route of administration. The dose range can be about 0.01 to about 200 milligrams per kilogram of body weight, more preferably about 0.1 to about 25 milligrams per kilogram of body weight, and most preferably about 1 to about 10 milligrams per kilogram of body weight. The human adult dose is in the range of about 5 to about 1400 milligrams daily, given either as a single dose or in 3 or 4 divided doses. Veterinary dosages correspond to human dosages with the amounts administered being in proportion to the weight and metabolic rate of the animal as compared to adult humans.

Concentrations for the in vitro contacting of animal cells are about $1 \times 10^{-8}$ molar to about $1 \times 10^{-3}$ molar for cell concentrations of about $2-5 \times 10^6$ cells per milliliter. More preferably, the concentration is about $1 \times 10^{-7}$ molar to about $1 \times 10^{-4}$ molar, and still more preferably about $3 \times 10^{-6}$ molar to about $3 \times 10^{-5}$ molar at the same cell concentrations. A composition for contacting the animal cells can be a solid or a liquid. The isoxanthopterin derivative can be admixed as a suspension of solid isoxanthopterin derivative in a solid or liquid physiologically tolerable carrier, or dissolved as a solute or suspended in the carrier, or a combination thereof.

Physiologically tolerable carriers are well known in the art. Exemplary of liquid carriers are sterile aqueous solutions that can contain no materials in addition to the active ingredient and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose and other solutes. These latter carries are exemplified by Ringer's injection, dextrose injection, dextrose and sodium chloride injection and lactated Ringer's injection.

Liquid compositions can also contain liquid phases in addition to and to the exclusion of water. Exemplary of such additional liquid phases are glycerin, vegetable oils such as cottonseed oil or sesame oil, and water-oil emulsions.

Exemplary solid carriers include those materials usually used in the manufacture of pills or tablets, and include corn starch, lactose, dicalcium phosphate, thickeners such as tragacanth and methylcellulose U.S.P., finely divided $SiO_2$, polyvinylpyrrolidone, magnesium stearate and the like. Additionally, the solid carrier can include biodegradable and nonbiodegradable polymers, polypeptide carriers, affinity carriers such as AFFI-GEL 601 (phenyl boronate resin available from Bio-Rad Laboratories, Richmond CA), and liposomes as are known in the art. Antioxidants such as methylparaben and proplyparaben can be present in both solid and liquid compositions, as can sweeteners such a cane or beet sugar, sodium saccharin, sodium cyclamate and the dipeptide methyl ester sweeteneer sold under the trademark NUTRASWEET (aspartame) by G. D. Searle Co.

Contact between the composition and animal cells is maintained for a time period sufficient for the contacted cells manifest the modulation of their cellular response. Modulation of cellular response (activity) can itself be manifest in enhanced antibody secretion, enhanced T helper activity, enhanced cytokine production, and the like.

For use in vivo, contact between animal cells and optimal concentrations of the composition is typically maintained for a time period sufficient for the animal to clear the isoxanthopterin derivative from its body as by metabolism, excretion or both processes. That time period can be longer than that required for a cellular response to be manifest. Contact with an individual unit dose is thus typically maintained for a time period of about one day to about seven days. Continual contact can be advantageous for an immunodeficient animal host.

Contact in vitro can be maintained for a period of time sufficient for one of the before-described cellular functions to become manifest as determined by standard assay techniques. Such maintenance times typically take about one to about seven days of time, and more usually about 2 to about 4 days.

C. Modulated Cellular Responses

1. In vitro adjuvanticity

Contacting animal antibody-producing cells with a composition useful herein provides an adjuvant effect on the primary antibody response to SRBC and other immunogens (antigens) when evaluated in vitro. The immune response-modulating composition and effective amount of immunogen (sheep red blood cells; SRBC) are typically admixed to contact the cells substantially simultaneously. The words "antigen" and "immunogen" are used interchangeably.

At optimal concentration, a composition containing an effective amount of a useful isoxanthopterin derivative enhances the response to SRBC by about 2-to 6-fold. The effect is dose dependent. Enhancement of the antibody response cannot be accounted for by the additive effects of the specific response to SRBC and the polyclonal response to the isoxanthopterin derivative.

The adjuvant effect of compositions containing a useful isoxanthopterin derivative is exerted on immunogen-experienced (primed) as well on naive cells. Both responses are enhanced by contacting the cells with compositions containing an effective amount of isoxanthopterin derivative. This adjuvant effect is dependent upon the concentration of immunogen added to culture.

While immune responses; i.e., responses of B lymphocytes or B cells, are observed to be enhanced at all immunologically effective doses of immunogen, the degree of enhancement is usually greatest at optimal or near optimal immunogen concentrations. Additionally, adjuvanticity of isoxanthopterin derivatives is synergistic with immunogen and not just due to the sum of independent immunogen-specific and polyclonal (non-specific) responses.

Enhancement of antibody produced by compositions containing an isoxanthopterin derivative involves not only naive, immunogen-inexperienced B cells, but also immunogen-experienced or memory B cells, as already noted. Thus, the primary IgM as well as the secondary IgM and IgG responses to immunogen (antigen) are augmented by contacting B cells with a composition containing an effective amount of an isoxanthopterin derivative as active ingredient, and maintaining that contact as discussed herein.

For memory responses, B cells are primed by treatment with an effective, priming, amount of an immunogen, as is well known. That priming treatment can be in the presence or absence of an immune response-modulating composition. When contacted in the presence of such a composition, treatment of the B cells with a priming amount of immunogen is preferably substantially simultaneous; i.e., within about 12 hours, with contacting of the cells with a composition useful in this invention. More preferably, the immunogen is included in the immune response-modulating composition, unless its effect is impaired by being in that composition, as by denaturation.

A modulated cellular response can thus be obtained by contacting B cells substantially simultaneously with an effective, priming amount of immunogen and an immune response-modulating composition useful herein, followed, after a primary immune response is obtained, by an additional contacting of the primed cells with a further effective amount of immunogen (antigen) alone or substantially simultaneously with a further amount of immune response-modulating composition.

When the B cells are primed in the absence of a composition useful herein, adjuvanticity can be demonstrated when the primed cells are again treated with a further effective amount of immunogen substantially simultaneously with those primed cells being contacted with a composition useful herein. A modulated cellular response can thus be manifest by treating B cells that are primed to an effective, priming amount of immunogen with a further, effective amount of immunogen and an immune response-modulating composition useful herein that is contacted with the B cells at preferably substantially the same time (within about 12 hours) as those cells are treated with the second, effective amount of immunogen.

Isoxanthopterin derivative-containing compositions useful herein are thought to enhance the primary humoral immune response by acting directly upon the B cell and/or the immunogen-presenting cell. Thus, use of these derivatives enhances the antibody response mounted against T-independent antigens; i.e., responses that involve B cells and immunogen-presenting cells. In addition, compositions containing an isoxanthopterin derivative can replace the need of B cells for T helper cells, as discussed hereinafter, and therefore exert their adjuvant effect in cultures initiated in the absence of intact, functional T cells. A replacement of T cells with T cell helper activity contained in mixed lymphocyte culture (MLC) supernates does not diminish the ability of an isoxanthopterin derivative to augment the antibody response.

Still further, the synergy observed between the soluble T cell signal contained in MLC supernate and the isoxanthopterin derivative-containing composition indicates that the signal supplied by each is qualitatively distinct. This synergy is observed over a range of supernate concentrations, indicating that the isoxanthopterin derivative is not simply providing more of the same "signal" that T cells provide. A comparable degree of synergy can be observed when such B cell cultures are supplemented with T cells rather than with T cell-like supernates (which are in fact T cell derived), and are contacted in the presence of immunogen with an isoxanthopterin derivative-containing composition useful in this invention.

T cell-mediated effects of the adjuvanticity of isoxanthopterin derivatives are not ruled out by the observation of T-independence for that adjuvanticity; i.e., the existance of a T cell-independent fact does not bear upon the existance of a T cell-dependent phase. Thus, more substantial enhancement can be observed from a composition containing the isoxanthopterin derivative under conditions of stimulation with low doses of T-dependent and T-independent type 2 antigens (T cell dependent situations) than with T-independent type 1 antigens (more completely T cell-independent), which suggests the presence of a T cell-dependent component. Moreover, isoxanthopterin derivatives are thought to act (either directly or indirectly) on precursors of T helper cells to increase the ability of a population of such cells to support an antibody response to immunogen.

2. In vivo modulation of immune response

Immunopotentiating effects on the primary antibody (B cell) response to SRBC in vivo are observed when a liquid composition containing an isoxanthopterin derivative useful herein is contacted with animal cells as by injecting the composition into CBA/CaJ mice thirty minutes after injection of the SRBC immunogen; i.e., substantially simultaneously. Relatively high dosages, e.g., about 2.5 milligrams per animal (about one-tenth gram per kilogram), are tolerated by the animals.

Immunogen dose dependency in the above mice to adjuvant effects of a constant level of the isoxanthopterin derivative injected intraperitoneally (i.p.) are compared with normal saline (NS) i.p. injections as a control. While there is an enhancement in the immune response at all useful (effective) levels of immunogen injection, typically, the enhancement becomes greater as the magnitude of the underlying response increases.

In vivo modulation of animal cellular responses as in the above-described primary immunization can also be effected as described before in relation to in vitro modulation of secondary immune responses of B cells.

3. T cell-replacing activity

A method of this invention can be used to substitute for T cells in the antibody response to a T-dependent immunogen. Here, T cells are depleted in vitro by treatment with complement and monoclonal anti-thy 1.2 antibodies and are cultured with or without SRBC as immunogen in the presence of compositions containing incremental concentrations of an isoxanthopterin derivative. Under these conditions, isolated B cell cultures are unable to respond to immunogen unless supplemented with a T cell-like signal, such as is contained by a composition containing an effective amount of an isoxanthopterin derivative. The modulated cellular response is dose-dependent as well as immunogen-dependent. In addition, this response cannot be attributed to nonspecific polyclonal activation of B cells.

Use of a method of this invention can provide a T cell-like signal to immunogen-stimulated B cells, supplanting the need for T cells altogether under conditions of an otherwise T-dependent response. Thus, supplementation of murine B cell cultures, depleted of thy 1.2-bearing T cells, with a composition containing an effective amount of an isoxanthopterin derivative replaces the requirement for T helper cells in the generation of a primary antibody response to SRBC. This occurs whether splenocytes are depleted of T cells by in vitro treatment with monoclonal anti-thy 1.2 antibodies and complement, or by in vivo injection of rabbit anti-mouse thymocyte serum (ATS) followed by in vitro treatment with ATS, anti-thy 1.2, anti-Lyt 1, and anti-Lyt 2 and complement as described by Harwell et al., J. Exp. Med. 152:893 (1980).

The mechanism of action of a composition of this invention is thought to be distinct from that of T cell-derived lymphokines and the T cell-replacing (or B cell stimulating) activity contained therein. This is shown by the synergistic effects of an isoxanthopterin derivative and T helper factor generated in MLC supernates wherein the anti-SRBC plaque forming cells (PFC) response supported by the supernates is amplified by addition of compositions containing an effective amount of an isoxanthopterin derivative.

4. Adjuvanticity by oral administration

Adjuvanticity of the compositions of this invention administered by in vivo i.p. or subcutaneous injection was discussed hereinbefore. Adjuvanticity of the compositions of this invention that are administered orally through a tube extending into the stomachs of the animals or by use of a round-tipped feeding needle extending into the esophagus of each animal can also be shown.

Here, SRBC are injected i.p. and the PFC determinations are made seven days after the initial i.p. injection of the SRBC. The compositions useful herein containing an effective amount of isoxanthopterin derivative are administered perorally within either the same 24-hour time period as the immunogenic dose of SRBC or 72 hours thereafter. Administration of a composition of this invention to contact the animal cells provides an enhanced primary response to the immunogen whether contacted with the animal cells within the same 24-hour period that those cells were subjected to the immunogen, or 72 hours thereafter.

For in vitro contacting, the cells are typically cultured in a medium that contains the isoxanthopterin derivative at a before-described concentration. For in vivo contacting, the composition is administered to the animal one or more times and is maintained in the animal until the last-administered dose is cleared from the animal's body, and thereby from contact with the animal's cells, by natural bodily processes as discussed before.

D. Best Mode For Carrying Out The Invention

Example 1.

Tablets

Tablets are compounded from the following ingredients:

|  | Parts by Weight |
| --- | --- |
| 8-(1'-Beta-D-ribofuranosidyl) isoxanthopterin | 0.5 |
| Lactose, powdered | 37.4 |
| Corn starch, dry | 35.5 |
| Finely divided $SiO_2$ | 5.6 |
| Polyvinylpyrrolidone | 0.6 |
| Magnesium stearate | 0.4 |
|  | 80.0 |

The isoxanthopterin derivative is thoroughly admixed with the lactose, 25.0 parts by weight of the corn starch, and 4.0 parts by weight of the $SiO_2$. The resulting admixture is then uniformly moistened with a 5% ethanolic solution of polyvinylpyrrolidone. The moist mass is then passed through a one-millimeter mesh screen to produce a granulate. The produced granulate is dried for about 24 hours at 60° C. in a drying chamber. The dried granulate is again passed through a one-millimeter mesh screen. 70.0 Parts of the obtained granulate are admixed in a suitable mixer with a mixture consisting of the remainder of the $SiO_2$, the remainder of the corn starch and all of the magnesium stearate, which mixture previously had been passed through a one-millimeter mesh screen. The thus-obtained admixture is then pressed into tablets weighing 800 milligrams each and containing 5 milligrams of the isoxanthopterin.

Example 2

Starch Capsules

Capsule contents are compounded from the following ingredients:

|  | Parts by Weight |
| --- | --- |
| 6-Carboxy-8-(1'-beta-D-glucopyranosidyl)-isoxanthopterin | 1.0 |
| Lactose | 450.0 |
| Corn Starch | 549.0 |
|  | 1000.0 |

The isoxanthopterin derivative is gradually admixed with the lactose. When all of the lactose has been admixed, the obtained admixture is blended with the corn starch. The resulting blend is then filled into capsules holding 1.0 gram of the blend. Each capsule contains 1.0 milligram of the isoxanthoperin derivative.

Example 3

Tablets

A lot of 10,000 tablets, each containing 50 milligrams of 6-methyl-8-(1'-beta-D-deoxyribofuranosidyl)-isoxanthopterin, is prepared from the following types and amounts of ingredients:

| | |
| --- | --- |
| 6-Methyl-8-(1'-beta-D-deoxyribofuranosidyl)isoxanthopterin | 500 grams |

-continued

| | |
|---|---|
| Dicalcium Phosphate | 1000 grams |
| Methyl cellulose, U.S.P. (15 cps) | 75 grams |
| Talc | 150 grams |
| Corn Starch | 250 grams |
| Magnesium stearate | 25 grams |
| | 2000 grams |

The isoxanthopterin derivative and dicalcium phosphate are mixed well, granulated with 7.5 percent solution of methyl cellulose in water, passed through a No. 8 screen (U.S. Standard Sieve Series) and dried carefully. The dried granules are passed through a No. 12 screen (U.S. Std. Sieve Series), mixed thoroughly with the talc, starch and magnesium stearate, and compressed into tablets.

These tablets are useful for enhancing antibody production when administered perorally at a dose of one to three tablets about every six to eight hours.

Example 4

Injectable Preparation

A sterile preparation suitable for subcutaneous or intracavitary injection and containing 50 milligrams of 6-carboxyethyl-8-(1'-beta-D-ribofuranosidyl)isoxanthopterin in each milliliter of ingredients is prepared from the following types and amounts of ingredients:

| | |
|---|---|
| 6-Carboxyethyl-8-(1-beta-D-ribofuranosidyl)isoxanthopterin | 5 grams |
| Physiological saline | 98 milliliters |
| Cottonseed oil (or sesame oil) | 2 milliliters |

The isoxanthopterin derivative and saline are admixed and sonicated for a period of time sufficient to provide a substantially homogenous dispersion. The cottonseed oil (or sesame oil) is thereafter admixed and the new admixture is similarly homogenized to provide an emulsion. After emulsification, one to three percent of the final volume of this sterile preparation are injected subcutaneously or intraperitoneally once a week to enhance humoral immunity.

Example 5

Aqueous Preparation for Oral Use

An aqueous preparation for oral use containing in each 5 milliliters (1 teaspoon) 5 milligrams of 6-carboxy-8-(1'-beta-D-glucopyranosidyl)isoxanthopterin is prepared from the following ingredients:

| | |
|---|---|
| 6-Carboxy-8-(1'-beta-D-glucopyranosidyl)-isoxanthopterin | 1.0 grams |
| Methylparaben, U.S.P. | 0.75 grams |
| Propylparaben U.S.P. | 0.25 grams |
| Saccharin sodium | 1.25 grams |
| Cyclamate sodium | 0.25 grams |
| Glycerin | 300 milliliters |
| Tragacanth powder | 1.0 grams |
| Orange oil flavor | 1.0 grams |
| F.D. and C. orange dye | 0.75 grams |
| Deionized water, q.s. to | 1000 milliliters |

A dose of one teaspoon two to four times per day is useful for enhancing humoral immunity.

Cell Contacting Conditions

Lymphocyte cultures

The serum-containing culture medium is prepared to contain the following per 100 millimeters: 91.9 milliliters RPMI 1640 (Flow Laboratories, Inc., Rockville, MD), 0.1 milliliters of 100×glutamine, 1.0 milliliter of 100×sodium pyruvate, 1.0 milliliter of 50×nonessential amino acids, 1.0 milliliter of water contain $10^4$ units of penicillin G and $10^4$ micrograms of streptomycin, and 5.0 milliliters of a supportive lot of fetal calf serum (FCS). These ingredients are admixed to apparent homogeneity. Spleen cell suspensions and populations enriched for splenic B cells are prepared as described in Goodman et al., *J. Immunol.*, 121: 1905 (1978).

For evaluation of the primary humoral immune response to sheep erythrocytes (SRBC), $5 \times 10^6$ to $10^7$ murine spleen cells are cultured in 1.0 milliliter of 5% FCS-containing medium for 4 or 5 days in the presence of immunogen. Cells are incubated in culture trays (3424, Costar, Cambridge, MA) at 37° C. in a humidified atmosphere of 10% $CO_2$ in air using tissue culture boxes (CBS Scientific, Del Mar, CA) that are rocked at a frequency of 7 cycles per minute. Pooled SRBC are available from the Colorado Serum Co., Denver CO.

Assay of plaque forming cells (PFC)

PFC secreting antibodies against SRBC are evaluated after 4 or 5 days of culture using a modification of the hemolytic plaque assay of Jerne and Nordin, *Science*, 140:405 (1963).

Mice

CBA/CaJ mice, 8–16 weeks of age, are purchased from the Jackson Laboratory, Bar Harbor, ME. All mice are maintained on Wayne Lab Blox F6 pellets (Allied Mills, Inc., Chicago, IL) and chlorinated water acidified with HCl to a pH value of 3.0.

Cell preparations

Spleen and thymus cell suspensions are prepared as described in Goodman et al., *J. Immunol.*, 121:1905 (1978). Spleen cells enriched for T lymphocytes are prepared by passage through nylon wool (NW) columns according to the protocol of Julius et al., *Eur. J. Immunol.*, 3:645 (1973). B cell-enriched populations are prepared by treating $10^8$ spleen cells with a 1:1000 dilution of monoclonal anti-Thy 1.2 antibody (New England Nuclear, Boston, MA) for 30 minutes at 4° C. Treated cells are centrifuged at 280×gravity for 10 minutes, antibodies are removed, and the cells are resuspended in a 1:6 dilution of CBA RBC-absorbed guinea pig complement at 37° C. for 45 minutes. Cells are then washed and cultured as described before.

Materials

Isoxanthopterin-8-beta-D-ribonucleoside was a gift of Dr. Wolfgang Pfleiderer, University of Konstanz, Konstanz West Germany. 8-Oxoguanosine (8-oxoGuo) was a gift from Dr. Roland Robins, ICN Pharmaceuticals, Costa Mesa, CA. Human IL-2, lot 1464-52, was obtained as a partially purified preparation from Electro-Nucleonics, Inc., Silver Springs MD. This preparation was found to be free of interferon-gamma activity.

Injections

Mice were injected i.p. with a suspension of washed SRBC at different concentrations in saline. At various times thereafter, different amounts of isoxanthopterin derivatives are injected i.p. or subcutaneously. The isoxanthopterin derivative is typically injected as a suspension in saline, in a water-oil emulsion, or in 10 mg/ml of sodium carboxymethyl cellulose (CMC) in normal saline (NS) or physiologic saline. For oral feeding studies, mice are intubated with poly(propylene) catheters extending from the mouth to the stomach, or with a round-tipped 20 gauge feeding needle as discussed before, and the measured amounts of compositions are introduced therethrough.

Example 6
Enhancement of Primary Antibody Response $5\times10^6$ Viable CBA/CaJ mouse spleen cells were cultured in 1 ml of serum-containing medium in the presence or absence of SRBC with incremental amounts of 8-(1'-beta-D-ribofuranosidyl)isoxanthopterin present over a concentration range of zero (None) through $1\times10^{-4}$ molar. PFC to SRBC were counted after 4 days of culture.

The results of two studies using the murine system as described hereinbefore are shown in Table 1, below.

TABLE 1

Adjuvanticity of Isoxanthopterin-8-beta-D
Riboside on the Murine
Primary Antibody Response

| Antigen[1] | Nucleoside[2] | Direct Anti-SRBC PFC/Culture | |
|---|---|---|---|
| | | Study 1 | Study 2 |
| None | None | 62 | 35 |
| SRBC | None | 468 | 495 |
| | Isox. Rib. at | | |
| SRBC | $10^{-8}$ | 638 | 418 |
| SRBC | $10^{-7}$ | 773 | 948 |
| SRBC | $10^{-6}$ | 778 | 660 |
| SRBC | $10^{-5}$ | 490 | 540 |
| SRBC | $10^{-4}$ | 208 | 178 |
| | 8-oxoGuo at: | | |
| SRBC | $3\times10^{-4}$ | 6217 | — |

[1] $5\times10^6$ SRBC used as antigen per culture.
[2] Nucleosides are listed as being absent (None) or at a concentration in moles per liter, e.g., $10^{-5}$ Isox. Rib. = isoanthropterin riboside; 8-oxoGuo = 8-oxoguanosine.

As can be seen, a dose-dependent enhancement of PFC in the presence of SRBC and isoxanthopterin derivative over those of the cultures containing the SRBC alone are noted. The activity of this compound at a concentration as low as $10^8$ molar was particularly surprising.

Example 7
Enhancement of Secondary Antibody Response $10^7$ Viable SRBC-primed CBA/CaJ mouse spleen cells are cultured in serum-containing medium in the presence or absence of variable concentrations of 8-(1'-beta-D-ribofuranosidyl)isoxanthopterin with $6\times10^5$ pooled SRBC per ml of culture. Direct PFC to SRBC are determined after 4 days of culture. Similar cultures are prepared as controls using the same incremental amounts of SRBC, but lacking the isoxanthopterin derivative.

PFC are increased in the cultures containing both the isoxanthopterin and SRBC as compared to cultures containing SRBC above.

Use of 6-methyl-8-(1'-beta-D-ribofuranosidyl)isoxanthopterin and 6-carboxy-8-(1'-beta-D-ribofuranosidyl)isoxanthopterin provides similar results.

Example 8
In Vivo Modulation of Immune Response

CBA/CaJ mice are injected with $6\times10^6$ SRBC intraperitoneally, and three days later with incremental amounts of 6-methyl-8-(1'-beta-D-ribofuranosidyl) isoxanthopterin in CMC. Concentrations of zero through 2.5 milligrams per animal are used. Assessment of direct PFC to SRBC 5 days thereafter shows a dose-dependent enhancement of the antibody response.

Similar results are obtained using 8-(1'-beta-D-ribofuranosidyl)isoxanthopterin and 6-carboxy-8-(1-beta-D-ribofuranosidyl)isoxanthopterin as the isoxanthopterin derivative.

Example 9
In Vitro Enhancement of Human Primary Immune Response

Human peripheral blood lymphocytes (PBL) were prepared from normal heparinized venous blood by Ficoll-diatrizoate density gradient centrifugation. PBL were depleted of suppressor T cells bearing the histamine type 2 receptor by adhering them to the surfaces of histamine-rabbit albumin-coated plastic petri dishes (Cell-ect No. 2 kit; Seragen, Boston, MA) and by recovering the nonadherent cells by panning as described by Wysocki and Sato, Proc. Natl. Acad. Sci. USA, 75:2844 (1978) and modified by Cavagnaro and Osband, Biotechniques, January/February:30 (1983).

The tissue culture medium employed in these studies was prepared as follows: One hundred milliliters (ml) contained 87.9 ml RPMI 1640 (Flow Laboratories, Rockville, MD), 0.1 ml $100\times$ glutamine, 1.0 ml of 1.0 M HEPES buffer (Microbilogical Associates, Betheseda, MD), 1.0 ml of water containing $10^4$U of penicillin G and $10^4$micrograms of streptomycin, and 10 ml of fresh autologous heat-inactivated plasma. For evaluation of the primary humoral immune response to SRBC, lymphoid cells were cultured at a density of $2\times10^6$/ml in a volume of 1.0 ml containing $5\times10^6$ SRBC as antigen (Colorado Serum Co., Denver, CO) together with IL-2 and the isoxanthopterin ribonucleoside.

Enumeration of plaque-forming cells (PFC) that secrete antibodies against SRBC was accomplished after 6 days of culture by using a modification of the hemolytic plaque assay of Jerne and Nordin, Science 140:405 (1963). The cells were brought up in complete medium before plaquing; they were plaqued in standard low $M_r$ agarose (Bio-Rad Laboratories, Richmond, CA), and were incubated in SRBC-absorbed guinea pig complement for 1 hour after a 1.5-hour incubation without complement.

The results of two studies are shown in Table 2, below.

TABLE 2

Adjuvanticity of Isoxanthopterin-8-beta-D-
Ribonucleoside on the Human
Primary Antibody Response

| Antigen[1] | Nucleoside[2] | Direct Anti-SRBC PFC/Culture[3] | |
|---|---|---|---|
| | | Study 1 | Study 2 |
| None | None | 7 | 12 |
| SRBC | None | 5,383 | 363 |
| | Isox. Rib. at | | |
| SRBC | $10^{-8}$ | 5,258 | — |
| SRBC | $10^{-7}$ | 6,017 | — |
| SRBC | $10^{-6}$ | 5,483 | — |
| SRBC | $10^{-5}$ | 7,592 | 665 |
| SRBC | $3\times10^{-5}$ | — | 248 |
| SRBC | $10^{-4}$ | 32,000 | 180 |
| SRBC | $3\times10^{-4}$ | — | 230 |
| | 8-oxoGuo at: | | |
| SRBC | $3\times10^{-4}$ | — | 1175 |
| SRBC | $10^{-3}$ | 10,100 | — |

[1] SRBC used as antigen at $5\times10^6$ cells per culture.
[2] Nucleosides are listed as being absent (None) or at a concentration in moles per liter, e.g., $10^{-5}$ Isox. Rib. = isoanthopterin riboside; 8-oxoGuo = 8-oxoguanosine.
[3] Direct anti-SRBC plaque-forming cells (PFC) per culture were determined as described before using PBL from two different human donors.

As can be seen from the above data, a dose-dependent antigen-specific enhancement was obtained with isoxanthopterin ribonucleoside. The results obtained were found at a higher concentration of the isoxanthopterin derivative than was optimal in the mouse system of Example 6. These results are consistent with results in murine and human systems observed using 8-substituted guanosines. See, Goodman and Hennen, *Cell,* 102:395 (1986) and Goodman and Weigle, *J. Immunol.,* 135:3284 (1985).

Example 10
T Cell Replacing Activity $4 \times 10^6$ Viable CBA/CaJ mouse splenic cells are treated first with complement-fixing monoclonal antibodies that immunoreact with thy 1.2 antigens of T cells and second with complement to lyse any T cells present (New England Nuclear, Boston, MA). The cells so treated are thereafter grown with or without SRBC as immunogen in serum-containing media further containing incremental amounts of 8-(1'-beta-D-ribofuranosidyl)isoxanthopterin ranging in amount from zero through $10^{-4}$ molar. Direct PFC to SRBC are determined 4 days thereafter. The results of this study indicate that the presence of the isoxanthopterin derivative assists in inducing a B cell response to the immunogen, and the result induced is dose-dependent. Thus, contacting the unlysed splenic cells (i.e., B cells) with a composition useful herein provides a T cell-like "signal" to those unlysed cells.

Similar results are obtained using 6-methyl-8-(1'-beta-D-ribofuranosidyl)isoxanthopterin and 6-carboxy-8-(1'-beta-D-ribofuranosidyl)isoxanthopterin to replace the above isoxanthopterin derivative.

The present invention has been described with respect to preferred embodiments. It will be clear to those skilled in the art that modifications and/or variations of the disclosed subject matter can be made without departing from the scope of the invention set forth herein.

What is claimed is:

1. A method of modulating an animal immune response comprising contacting animal cells with a composition containing a diluent amount of a physiologically tolerable carrier admixed with an immune response-modulating effective amount of an active ingredient that is an isoxanthopterin derivative whose structure conforms to that of the formula

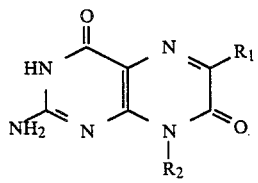

wherein $R_1$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo, lower alkoxy, phenyl-lower alkoxy, halo, mercapto, thioxo, lower alkylthio, lower alkyloylthio, phenyl-lower alkylthio, lower alkanoyl, carboxy, lower alkoxy carbonyl, lower alkylcarboxy, lower alkylene lower alkylcarboxylate, lower alkoxy lower alkyl carbonyl, and carboxamido and lower alkyl carboxamido in which the carboxamido group has the formula $CONR_3R_4$ wherein $R_3$ and $R_4$ are the same or different and are selected from the group consisting of hydrogen and lower alkyl or $NR_3R_4$ together form a heterocyclic ring having five or six atoms in the ring;

$R_2$ is a beta-bonded aldoglycoside radical selected from the group consisting of 1'-aldopentosidyl, 1'-aldonexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent, if present on one oxygen, is present on all available ring substituent oxygens;

the tautomers of said isoxanthopterin derivative; and the pharmaceutically acceptable salts of said isoxanthopterin derivative; and maintaining said contact for a time period sufficient for said cells to modulate their immune response.

2. The method in accordance with claim 1 wherein $R_2$ is selected from the group consisting of 1'-ribofuranosidyl, 1'-(2'-deoxy)ribofuranosidyl and 1-glucopyranosidyl radicals.

3. The method in accordance with claim 2 wherein the structure of said isoxanthopterin compound conforms to the formula

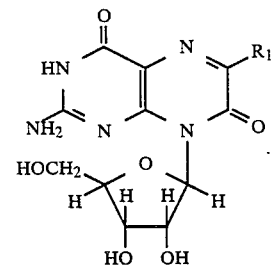

4. The method in accordance with claim 3 wherein $R_1$ is selected from the group consisting of hydrogen, methyl, and carboxy.

5. The method in accordance with claim 1 wherein the structure of said aldoglycosidyl radical conforms to the formula

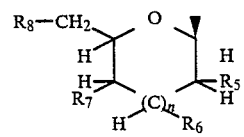

wherein n is zero or more;

$R_5$ is selected from the group consisting of hydrogen, hydroxy, lower alkoxy, benzyloxy, lower alkanoyloxy, and benzoxy;

$R_6$, $R_7$ and $R_8$ are the same and are selected from the group consisting of hydroxy, lower alkoxy, benzyloxy, lower alkanoyloxy, and benzoxy; and where $R_5=R_6=R_7=R_8$ when $R_5$ is other than hydrogen.

6. The method in accordance with claim 5 wherein n is zero, and $R_5$, $R_6$, $R_7$ and $R_8$ are hydroxy.

7. The method in accordance with claim 5 wherein n is 1, and $R_5$, $R_6$, $R_7$ and $R_8$ are hydroxy.

8. The method in accordance with claim 1 wherein said cells are leukocytes.

9. The method in accordance with claim 8 wherein said leukocytes are B lymphocytes.

10. The method in accordance with claim 9 including the additional step of treating said B lymphocytes with an effective amount of an immunogen prior to contact with said composition, said immunogen treatment priming said B-lymphocytes.

11. The method in accordance with claim 10 wherein said B lymphocytes are contacted with said composition in conjunction with an additional amount of an immunogen previously used to prime said B lymphocytes for an immune response.

12. The method in accordance with claim 9 wherein said B lymphocytes are contacted with said composition substantially simultaneously with an effective amount of an immunogen.

13. The method in accordance with claim 1 wherein the animal cells contacted with said composition are leucocytes.

14. The method in accordance with claim 13 wherein said animal cells are contacted in vitro.

15. A method of enhancing cellular immune responses of leucocytes comprising the steps of:
contacting leucocytes with a composition containing a diluent amount of a physiologically tolerable carrier admixed with an immune response-modulating effective amount of an active ingredient that is an isoxanthopterin derivative whose structure conforms to that of the formula

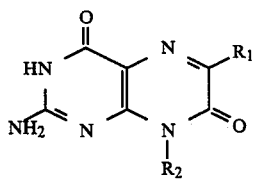

wherein
$R_1$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo, lower alkoxy, phenyl-lower alkoxy, halo, mercapto, thioxo, lower alkylthio, lower alkyloylthio, phenyl-lower alkylthio, lower alkanoyl, carboxy, lower alkoxy carbonyl, lower alkylcarboxy, lower alkylene lower alkylcarboxylate, lower alkoxy lower alkyl carbonyl, and carboxamido and lower alkyl carboxamido in which the carboxamido group has the formula $CONR_3R_4$ wherein $R_3$ and $R_4$ are the same or different and are selected from the group consisting of hydrogen and lower alkyl or $NR_3R_4$ together form a heterocyclic ring having five or six atoms in the ring;

$R_2$ is a beta-bonded aldoglycoside radical selected from the group consisting of 1'-aldopentosidyl, 1'-aldohexosidyl, mono-deoxygenated 1'-aldopentosidyl, and mono-deoxygenated 1'-aldohexosidyl and their O-substituted lower alkyl, lower alkanoyl, benzyl and benzoyl derivatives wherein an O-substituent, if present on one oxygen, is present on all available ring substituent oxygens;

the tautomers of said isoxanthopterin derivative; and
the pharmaceutically acceptable salts of said isoxanthopterin derivative; and
maintaining said contact for a time period sufficient for said leucocytes to modulate their immune responses.

16. The method according to claim 15 wherein the structure of said isoxanthopterin derivative conforms to the formula

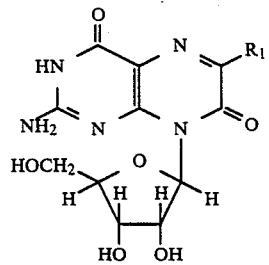

17. The method according to claim 15 wherein $R_1$ is selected from the group consisting of hydrogen, methyl and carboxy.

18. A method of enhancing the secretion of antibodies to a preselected immunogen comprising the steps of:
contacting immunoglobulin-producing cells with a composition containing a diluent amount of a physiologically tolerable carrier admixed with (a) an effective amount of a preselected immunogen to induce secretion of said antibodies and (b) an adjuvant amount of a isoxanthopterin derivative whose structure conforms to that of the formula

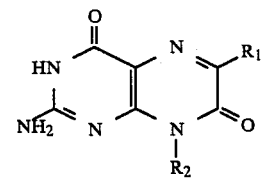

wherein
$R_1$ is a radical selected from the group consisting of hydrogen, lower alkyl, hydroxy lower alkyl, polyhydroxy lower alkyl, phenyl, phenyl-lower alkyl, lower alkyl phenyl, lower alkoxy phenyl, halophenyl, trifluoromethyl phenyl, hydroxy, oxo, lower alkoxy, phenyl-lower alkoxy, halo, mercapto, thioxo, lower alkylthio, lower alkyloylthio, phenyl-lower alkylthio, lower alkanoyl, carboxy, lower alkoxy carbonyl, lower alkylcarboxy, lower alkylene lower alkylcarboxylate, lower alkoxy lower alkyl carbonyl, and carboxamido and lower alkyl carboxamido in which the carboxamido group has the formula $CONR_3R_4$ wherein $R_3$ and $R_4$ are the same or different and are selected from the group consisting of hydrogen and lower alkyl or $NR_3R_4$ together form a heterocyclic ring having five or six atoms in the ring;

$R_2$ is a beta-bonded aldoglycoside radical selected from the group consisting of 1'-aldopentosidyl, 1'-aldohexosidyl, mono- deoxygenated 1'-aldopentosidyl, and mono-deoxygenated 1'-aldohexosidyl and their O-substituted lower alkyl, lower alkanoyl, benzyl and benzoyl derivatives wherein an O-substituent, if present on one oxygen, is present on all available ring substituent oxygens;

the tautomers of said isoxanthopterin derivative; and
the pharmaceutically acceptable salts of said isoxanthopterin derivative; and
maintaining said contact for a time period sufficient for said contacted cells to secrete antibodies to said immunogen.

19. The method according to claim 18 wherein said immunoglobulin-producing cells are primed to said preselected immunogen prior to said contacting step.

* * * * *

UNITED STATES PATENT AND TRADEMARK OFFICE
CERTIFICATE OF CORRECTION

PATENT NO. : 4,900,675

DATED : February 13, 1990

INVENTOR(S) : Michael G. Goodman

It is certified that error appears in the above-identified patent and that said Letters Patent is hereby corrected as shown below:

Column 1, after the title and before the heading "CROSS-REFERENCE TO COPENDING APPLICATION", insert the following paragraph:

--This invention was made with government support under Contract No. AI 15284 awarded by the National Institutes of Health. The government has certain rights in the invention.--

Signed and Sealed this

Eighteenth Day of January, 1994

Attest:

BRUCE LEHMAN

Attesting Officer

Commissioner of Patents and Trademarks